United States Patent
Eibofner

(12) 
(10) Patent No.: US 6,425,761 B1
(45) Date of Patent: Jul. 30, 2002

(54) DRIVE SYSTEM FOR DENTAL HANDPIECE

(75) Inventor: Eugen Eibofner, Biberach (DE)

(73) Assignee: Kaltenbach & Voigt GmbH Co., Biberach (DE)

( * ) Notice: Subject to any disclaimer, the term of this patent is extended or adjusted under 35 U.S.C. 154(b) by 30 days.

(21) Appl. No.: 09/717,273

(22) Filed: Nov. 22, 2000

Related U.S. Application Data

(63) Continuation of application No. PCT/EP99/03619, filed on May 26, 1999.

(30) Foreign Application Priority Data

May 26, 1998 (DE) .................................... 298 09 467 U
Jul. 22, 1998 (DE) .................................... 298 13 086 U

(51) Int. Cl.[7] .................................................. A61C 1/00
(52) U.S. Cl. .................................... 433/131; 433/132
(58) Field of Search ........................... 433/132, 114, 433/120, 126, 131

(56) References Cited

U.S. PATENT DOCUMENTS 4,966,552 A    10/1990   Gosner ........................ 433/132
6,164,831 A  * 12/2000   Matsui et al. ............ 433/132 X

FOREIGN PATENT DOCUMENTS

| DE | 2834099 C2 | 2/1980 |
|---|---|---|
| DE | 3215255 C2 | 8/1995 |
| DE | 4439799 C1 | 5/1996 |
| DE | 19604628 A | 8/1997 |
| DE | 19622486 C1 | 10/1997 |

OTHER PUBLICATIONS

"Zahnärztliche Behandlungsgeräte", DIN EN ISO 7494, Dec. 1997, cover sheet, plus 10 pages.

* cited by examiner

*Primary Examiner*—Nicholas D. Lucchesi
(74) *Attorney, Agent, or Firm*—Fitzpatrick, Cella, Harper & Scinto

(57) ABSTRACT

A drive system for dental handpieces, having a rotor (12) secured to a motor shaft (11), an anti-friction bearing system (13, 14), including an inner bearing race (17), an outer bearing race (18) and a plurality of rolling elements (19) arranged between the bearing races, and a coupling element (16) for coupling thereto a dental instrument (1) that is to be driven, the rolling elements consisting of a non-electroconductive material.

16 Claims, 4 Drawing Sheets

DRIVE SYSTEM FOR DENTAL HANDPIECE

CROSS REFERENCE TO RELATED APPLICATIONS

This is a continuation of International Application PCT/EP99/03619 filed May 26, 1999.

BACKGROUND OF THE INVENTION

1. Field of the Invention

The invention relates to a drive system for dental handpieces of the type which have a rotor secured to a motor shaft where the rotor is mounted by means of at least one anti-friction bearing having an outer race and an inner race and a plurality of rolling elements arranged between the races.

2. Description of the Related Art

Medical or dental handpieces generally comprise an instrument portion for receiving a dental tool, for example a turbo-drill, a drive motor for driving the rotating dental tool, and a hose portion that has a media-supply hose for supplying specific supply media for the operation of the dental tool, such as, for example, current, spray or cooling air, spray water, etc.

FIG. 7 shows, by way of example, the three individual components: the instrument portion 1 with the dental tool 5 rotatably mounted on the head portion 6, the drive motor 3 and the hose portion 2 with the media-supply hose 4, which components are coupled by being attached directly one after the other. Such a structure is known, for example, from DE-C2 28 34 099. An alternative kind of structure is shown in FIG. 8. The drive motor 3 here is a so-called motor cartridge which is held in a hollow space formed by the instrument portion 1 and the hose portion 2.

An electric motor, in particular a d.c. motor, as known from DE-A1 196 04 628 belonging to the applicant, is, for example, used as the drive motor. The drive motor substantially comprises a rotor magnet, which is rotatably mounted by way of a motor shaft, and a stator having a self-supporting stator air-gap winding which has free spaces for media lines that supply specific supply media to the dental instrument that can be coupled thereto. The motor shaft is mounted in a motor housing by means of a front and a rear motor bearing.

Usually, anti-friction bearing systems are used as the motor bearings, said anti-friction bearing systems being composed of an inner bearing race, an outer bearing race and a plurality of rolling elements that are arranged between the two bearing races, with both the bearing races and the rolling elements being formed of steel in a manner known per se. As an alternative to the d.c. motor that is described, it is also possible to use an a.c. motor.

In addition to an electric motor (d.c. motor or a.c. motor) it is also possible to use an air motor as the drive motor. Such a motor is, for example, disclosed in DE-C2 32 15 255 belonging to the applicant. As follows in particular from FIGS. 5 and 7 of this printed specification, the air motor that is formed as a a lamellar motor has a central shaft that is rotatably mounted in a circular chamber, which is offset in relation to the center, and has radial slots, in which lamellae are pressed radially outwards as a result of the action of the force of a spring so as to rest against the inner wall of the chamber. The shaft of the air motor is also mounted in the housing by means of anti-friction bearing systems.

Other known air motors have a rotor in the form of a turbine wheel against which a compressed-air flow can flow tangentially or along a secant.

Since, in contrast with the above electric motor, the air motor is basically suited to withstand repeated sterilization, the air motor can also be a fixed component part of the instrument portion. When an electric motor is used, on the other hand, the latter must be detachably connected to the instrument portion in order to separate it from the instrument portion for the sterilization process, since the electronic components of the electric motor do not generally withstand repeated sterilization at least on a permanent basis.

Furthermore, various safety regulations are to be followed in the case of dental handpieces. Thus for, example, DIN EN ISO 7494, December 1997, "Zahnärztliche Behandlungsgeräte" exists, laying down requirements and testing methods for dental treatment units irrespective of their design. Collected together under item 5.3 of this DIN-regulation inter alia there are electrical requirements, the observance of which is to guarantee that injuries to the patient and/or the personnel carrying out the treatment, for example as a result of an electric shock, are avoided.

Since the live components of dental handpieces extend into the drive motor, and the transmission elements of the handpieces including dental tools are mainly made of metal and thus are electro-conductive, expensive protective measures must be taken in the dental handpieces.

SUMMARY OF THE INVENTION

It is therefore an object of the present invention to provide a drive system of the kind mentioned by way of introduction in which further precautions for the observance of the electrical safety requirements are taken in a simple manner in order to increase further the safety of the patient and of the personnel carrying out the treatment.

This object is achieved by means an anti-friction system having rolling elements which consist of a non-electroconductive material. The use of steel anti-friction bearing systems with rolling elements that consist or are formed of non-electroconductive material guarantees electrical insulation between the stator or motor housing and rotor of the drive motor. As a result, current is prevented from being able to flow off by way of the ball bearings and the housing of the drive motor to the patient or to the personnel carrying out the treatment in the event of a defect of the drive motor.

Steel anti-friction bearing systems that have ceramic rolling elements (so-called hybrid anti-friction bearings) or fully ceramic anti-friction bearing systems are advantageously used to mount the motor shaft of the drive system. On account of the special material properties that ceramic materials have, this results in further advantages. The use of silicon nitride ($Si_3N_4$) for the rolling elements and possibly the bearing races is particularly advantageous here.

In this connection, in addition to the great electrical resistance in particular the lower specific gravity, the lower thermal conductivity, the clearly better resistance to chemicals and disinfectants and/or sterilizing agents, and the better temperature stability than steel are to be mentioned as advantageous material properties of ceramic materials.

Further configurations and developments of the present invention are disclosed and claimed herein.

BRIEF DESCRIPTION OF THE DRAWINGS

The invention is explained in greater detail in the following with the aid of preferred exemplary embodiments and with reference to the enclosed drawing, in which.

DETAILED DESCRIPTION OF THE PREFERRED EMBODIMENT

In the case of dental handpieces, a drive by way of a fluid, in particular air, and a drive by means of electric current are fundamentally different. The present invention can basically be used for both drive possibilities.

Figure 1:
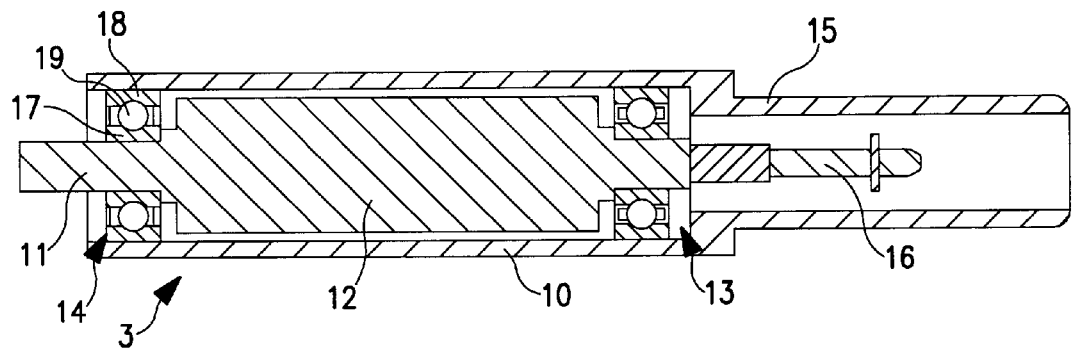
FIG. 1 shows a diagrammatic representation of a drive system in accordance with the present invention in section along its longitudinal axis.
Figure 7:
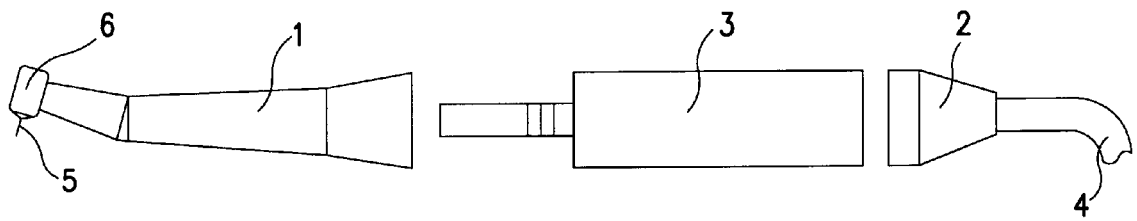
FIG. 7 shows a diagrammatic representation of a conventional dental handpiece.
Figure 8:
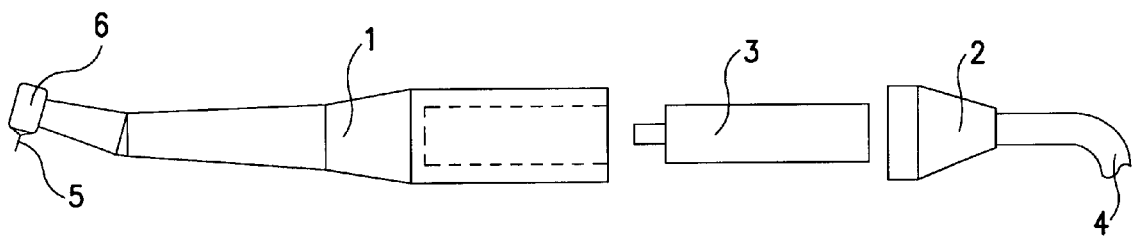
FIG. 8 shows a diagrammatic representation of a further conventional dental handpiece.

FIG. 1, in the first instance in quite a general manner, shows a diagrammatic representation of a drive system 3 (electric drive or air drive) in accordance with the invention. A rotor 12, which is secured to a central motor shaft 11, is arranged in a motor housing 10. The motor shaft 11 is rotatably mounted in the motor housing 10 by means of a front motor bearing 13 and a rear motor bearing 14. On the side that is turned towards the front motor bearing 13, the motor housing 10 has, furthermore, a coupling element 15, which advantageously is standardized, for coupling a dental instrument 1 that is to be driven. The coupling element 15 contains a coupling pin 16 that is connected to the motor shaft 11 in a rotationally secure manner and which engages with a corresponding driver pin of the instrument portion 1, when the instrument portion 1 is plugged thereon, and mechanically transmits the rotational movement of the motor shaft 11. By means of suitable mechanical connecting elements that are known per se, this rotational movement in the instrument portion 1 is transmitted further to the dental tool 5 that is held on the head portion 6 of the instrument portion 1.

The two motor bearings 13, 14 are each in the form of anti-friction bearing systems. They substantially consist of an inner bearing race 17, an outer bearing race 18 and a plurality of rolling elements 19 that are arranged between the two bearing races 17, 18 and which in particular are in the form of balls and render possible relative movement of the bearing races 17, 18 in relation to each other.

In accordance with the invention, when the anti-friction bearing systems 13, 14 are put together rolling elements 19 of a non-electroconductive material are inserted. This guarantees that there is electrical insulation between the stator or motor housing 10 and the rotor 12 of the drive motor 3. As a result, with simple means it is effectively possible to prevent current from being able to flow off by way of the ball bearings 13, 14 and the motor housing 10 to the patient or to the personnel carrying out the treatment in the event of a defect of the drive motor 3.

The use of rolling elements 19 made of a ceramic material has proved to be particularly advantageous when selecting the anti-friction bearing composition. In this connection, a choice can be made between a fully ceramic anti-friction bearing and a steel anti-friction bearing with ceramic rolling elements (a so-called hybrid anti-friction bearing). In any case, however, at least the rolling elements 19 are formed from a ceramic material.

Of the known ceramic materials that are available on the market, such as in particular nitrides, carbides and borides, silicon nitride ($Si_2N_4$) has proved to be the most suitable ceramic material for anti-friction bearings of the kind described above. Shaped bodies of silicon nitride can be produced by reaction-sintering, sintering, hot-pressing and high-temperature isostatic pressing, with combined manufacturing processes also being possible.

Various material properties with values typical of silicon nitride together with the corresponding typical values for conventional anti-friction bearing-steel are listed in the table below:

| Material properties | Unit | Silicon nitride | Anti-friction bearing steel |
|---|---|---|---|
| Density | $g/cm^3$ | 3.2 | 7.85 |
| Coefficient of linear expansion | $10^{-6} m/m\,°C$ | 3.2 | 11 |
| Modulus of elasticity at 20° C. | $kN/mm^2$ | 315 | 208 |
| Hardness HV10 at 20° C. | | 1700 | 700 |
| Bending strength at 20° C. | $N/mm^2$ | 700 | 2400 |
| Bending strength at 1000° C. | $N/mm^2$ | 700 | 0 |
| Thermal conductivity at 20° C. | $W/m\,K$ | 30–40 | 40–50 |
| Spec. electrical resistance at 20° C. | $\Omega\,mm^2/m$ | $10^{17}$–$10^{18}$ | $10^{-1}$–1 |
| Temperature use limit | °C. | ca.1000 | ca. 300 |
| Corrosion stability | | good | poor |
| Magnetism | | no | yes |

[from: "Fight mit harten Kugeln", R. Weigand, separate print of the sepcialist journal MASCHINE+WERKZEUG 22/1987-Konstruktion+Entwicklung 8]

In addition to the electrical insulating capacity already explained above, in the following a few further material properties shall be singled out and the advantages connected with them shall be discussed in comparison with the steel that is conventionally used for anti-friction bearing systems in drive systems for dental handpieces.

On account of the comparatively low density of ceramic material, during the rotational movement comparatively small centrifugal forces occur, this resulting in more favorable bearing stresses. Moreover, in addition less frictional resistance of the rolling elements 19 and thus less heat generation can be established, resulting in a longer service life of the anti-friction bearing. Furthermore, it has been shown in this connection that ceramic anti-friction bearings and hybrid anti-friction bearings even without lubrication of the bearing composition have longer service lives than steel anti-friction bearings. A longer service life is likewise promoted by the greater dimensional stability of the ceramic material in comparison with steel even at high temperatures.

Furthermore, the lower thermal conductivity of the ceramic material results in the heat, which has developed on account of the rotation of the rotor 12, being transported less easily outwards to the motor housing 10. This improved thermal insulation is advantageous in particular in the case of motor handpieces which the user holds in the hand.

The favorable corrosion stability and the good resistance to most chemical substances are advantageous in particular in the case of air motors 3 which are fixedly integrated in the instrument portion 1 of the dental handpiece and which together with the instrument portion are repeatedly sterilized.

The person skilled in the art will readily identify from the material properties of ceramic materials that are listed in the table given above and also from further known material properties of ceramic materials even further advantages which the use, in accordance with the invention, of ceramic or hybrid anti-friction bearings in drive systems for dental handpieces brings.

Figure 2:
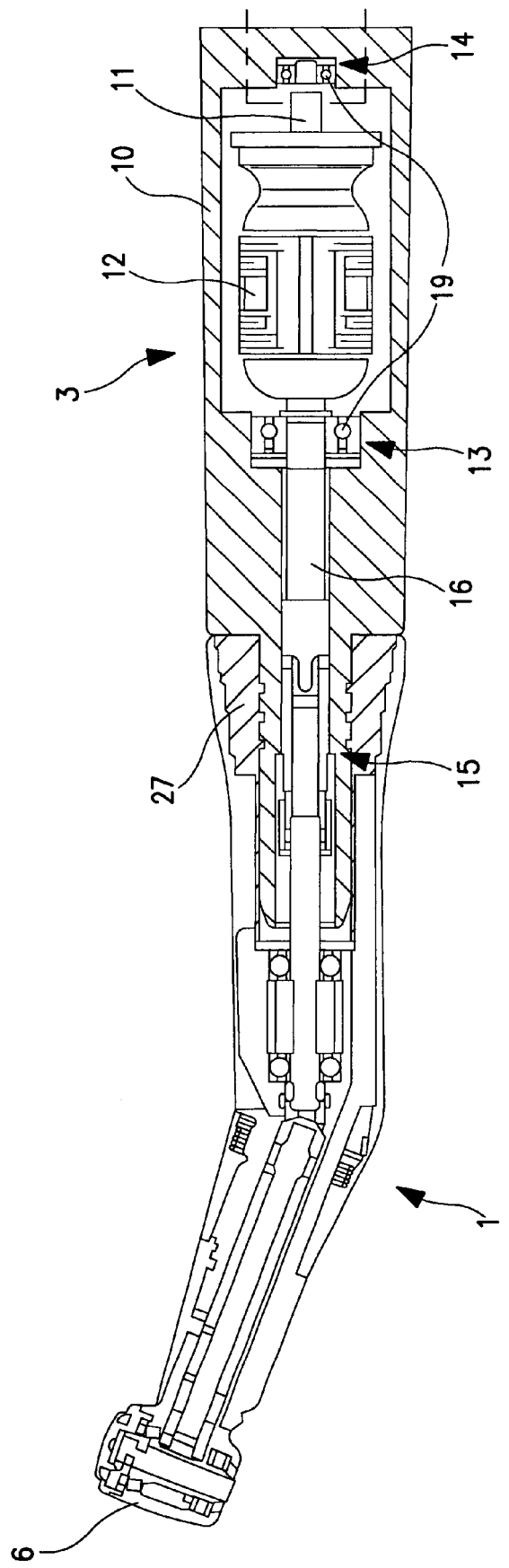
FIG. 2 shows a dental handpiece with a drive system in accordance with the present invention in section along the longitudinal axis.

A dental handpiece having the drive system 3, which is connected to the instrument portion 1, is shown in FIG. 2. The coupling 15, 16 has in this case in addition a circumferential coupling insulation 27 which consists of a non-electroconductive material, preferably a plastics material. As a result, the generally metal motor housing 10 is electrically insulated from the instrument portion 1 so that a further safety function exists for the patient, since no current can flow off by way of the motor housing 10 to the instrument portion 1 and possibly the dental tool 5.

In the following with the aid of FIGS. 3 and 4 the construction of an electric motor and an air motor as a drive system for a dental handpiece, for which the present invention is used respectively, shall be described in greater detail.

Figure 3:
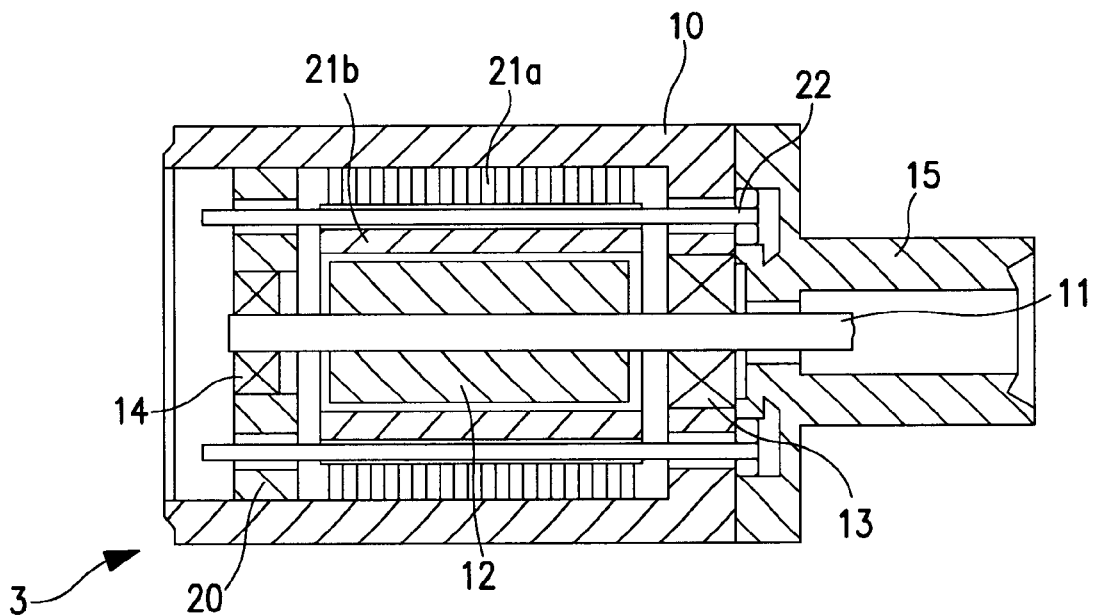
FIG. 3 shows a representation of an electric motor as a drive system in accordance with the present invention in longitudinal section.

The drive portions of the d.c. motor 3 shown in FIG. 3 are arranged in a motor housing 10, with there being connected to the motor housing 10 a coupling element 15 onto which a dental instrument 1 that is to be driven by the d.c. motor can be plugged. This coupling element 15 as a rule is a standardized coupling. The motor shaft 11 is rotatably mounted by means of a front motor bearing 13 and a rear motor bearing 14 in a rear bearing sleeve 20, with ceramic anti-friction bearings or hybrid anti-friction bearings in accordance with FIG. 1 being used for the two motor bearings 13, 14.

The rotor 12, which is secured to the motor shaft 11, is surrounded by a stator 21 which consists of a soft magnetic return ring 21a and a self-supporting stator air-gap winding 21b located therein, with the return ring 21a preferably being produced as a laminated iron return ring. The self-supporting stator air-gap winding 21b is packed or filled by injection-moulding with plastics material and has free spaces for the guidance of media lines 22 for supplying the dental instrument 1 that can be coupled thereto. Furthermore, the d.c. motor 3 is configured in such a way that after the coupling element 15 has been disassembled, the rotor 12 can be withdrawn laterally out of the motor housing 10 without any further disassembly measures so that the two anti-friction bearings 13, 14 are substantially more easily accessible in the case of a repair. A detailed description of such an electric motor 3 can be taken, for example, from DE-A1 196 04 628 which belongs to the applicant and has already been mentioned above.

Express reference may be made again at this point to the fact that the invention can be used and brings the advantages described above in like manner in the case of d.c. motors and in the case of a.c. motors.

Figure 4:
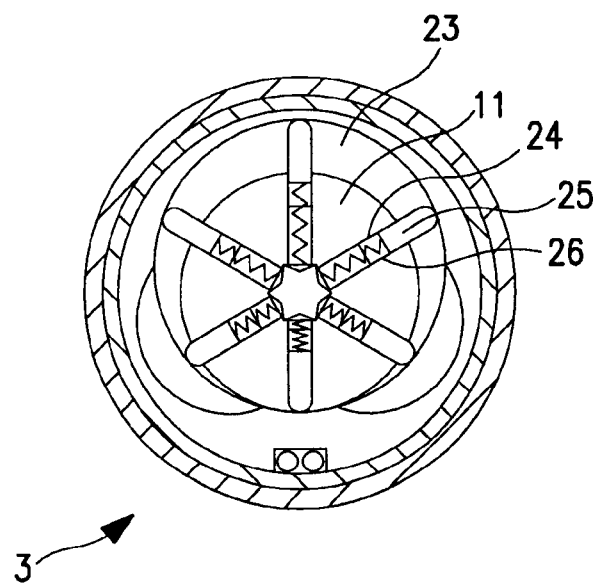
FIG. 4 shows a cross-sectional representation of an air motor as a drive system in accordance with the present invention.

The air motor 3 that is shown in cross section in FIG. 4 is formed as a lamellar motor in a manner known per se. The air motor 3 has a central motor shaft 11 which is rotatably mounted in a circular chamber 23 that is offset in relation to the center. Here as well ceramic anti-friction bearings or hybrid anti-friction bearings in accordance with FIG. 1 are used for mounting the motor shaft 11.

The motor shaft 11 has radial slots 24 in which respective lamellae 25 are pressed radially outwards as a result of the action of the force of a spring 26 so as to rest against the inner wall of the chamber 23. At a location that is offset somewhat in relation to the point at which the motor shaft 11 is closest to the inner wall of the chamber 23, air is supplied that acts on the lamellae 25 and turns the latter together with the motor shaft 11, with the air that is supplied leaving the chamber 23 at that point at which there is the greatest distance between the motor shaft 11 and the inner wall of the chamber 23. Depending on which side of the point of closest proximity the air is supplied, the motor shaft 11 is turned to the right or left. In a manner known per se the air motor 3 is formed in such a way that the air can be supplied to the chamber 23 both to the right and to the left of the point of closest proximity, with the supply taking place selectively either on the right or the left. A more detailed description of such an air motor 3 is disclosed, for example, in DE-C2 32 15 255 which belongs to the applicant and has already been mentioned above.

It is advantageous to associate a ring seal 31 with a motor bearing 13 and/or 14 so that foreign matter cannot reach the motor bearing 13 or 14. In this connection, within the scope of the invention the ring seal 31 can cooperate directly with the motor bearing 13, 14 or can cooperate indirectly therewith. The ring seal 31 is preferably arranged on the outside of the motor bearing 13, 14 in each case. Since, however, it is also possible for foreign matter or impurities to penetrate into the motor bearing 13, 14 from the respective inside, it is advantageous to arrange a ring seal 31 on the outside and inside respectively. Furthermore, it is possible for there to be such cases of installation in which the motor bearing 13, 14 is arranged in such a way, for example in an annular recess, that foreign matter or impurities can only penetrate into the motor bearing 13, 14 from one side, for example from the outside or from the inside. In such cases, it suffices if just the side of the motor bearing 13, 14 that is at risk is sealed.

Figure 5:
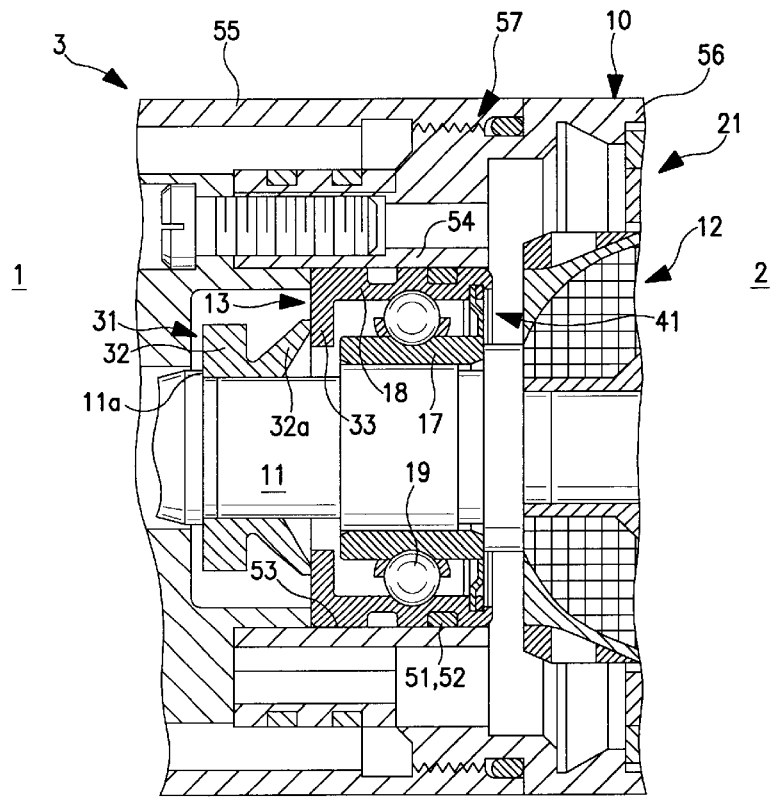
FIG. 5 shows a longitudinal portion of a modified configuration of a drive system in accordance with the invention in axial section.
Figure 6:
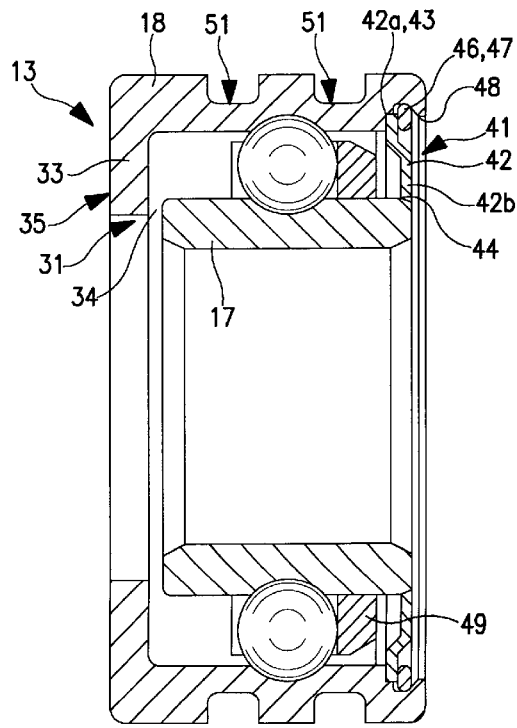
FIG. 6 shows a front anti-friction bearing of the drive system in accordance with FIG. 5 as a single structural unit in axial section.

The exemplary embodiment according to FIG. 5, in which identical or comparable parts are provided with the same reference symbols, presents a drive system 3 with an electric motor in the region of the motor bearing 13 which is arranged on the side of the motor that faces the instrument portion 1, which is not shown. In the case of this configuration, a sealing ring 32 is provided that cooperates with the inner or outer bearing race 17, 18 of the motor bearing 13 in a sealing manner. In the first case, in which the sealing ring 32 cooperates with the inner bearing race 17 (not shown), the sealing ring 32 sits so that it rests against a component that surrounds the motor shaft 11 with clearance of motion, and in the second case, in which the sealing ring 32 cooperates with the outer bearing race 18 in a sealing manner, the sealing ring 32 sits directly or indirectly on the motor shaft 11 so that in each of these cases a seal is provided either between the inner bearing race 17 and an annular portion surrounding the motor shaft 11 or between the outer bearing race 18 and, directly or indirectly, the motor shaft 11.

In the case of the present exemplary embodiment, associated with the motor bearing 13 there is an annular leg 33 that extends in a substantially radial manner and which can extend radially outwards from the inner bearing race 17 or radially inwards from the outer bearing race 18 and in each case ends close to the other bearing race or overlaps the latter. In order, on the one hand, to avoid friction and, on the other hand, if the bearing races 17, 18 are made of metal, in particular alloyed steel, to avoid an electrical connection, as previously described, and a flow of electric current, an annular gap 34 can be provided between the bearing races 17, 18, which gap in the case of electroconductive or metal bearing races 17, 18 is so large that no flow of electric current or spark-over can result. The inner and/or outer bearing race 17, 18 can also be made of non-electroconductive material, preferably of a ceramic material. The ceramic materials that have already been described are also suitable as such a ceramic material. In the case of the present exemplary embodiment, the axial distance between the bearing races 17, 18 amounts, for example, to 0.2 mm. The annular leg 33 and the bearing races 17, 18 preferably overlap each other, in which case if they are at a distance from each other they form a covering and if they rest against each other they form a seal. They can, however, also be arranged close together at their lateral edges.

The outer end face of the annular leg 33 forms a preferably planar or radial sealing face 35 for the sealing ring 32 which preferably touches the sealing face 35 with a sealing lip 32a or presses against it with a low level of axial elastic tension. The sealing lip 32a is pre-formed on and is in one piece with a ring base 32b which in the case of the present exemplary embodiment sits on the motor shaft 11 preferably with radial tension and, for example, rests against a shoulder 11a of the motor shaft and is restricted or secured to prevent its removal from the associated bearing race. In the case of the present exemplary embodiment, the sealing lip 32a diverges inwards in the form of a hollow cone, in which case it can enclose a cone angle of approximately 30° to 60°, in particular approximately 45°. On account of the, if applicable, elastic abutting arrangement of the sealing ring 32 or the sealing lip 32a that is made of elastic material, it is guaranteed that the annular gap between the bearing races 17, 18 is sealed.

Within the scope of the invention the solidity of the sealing lip 32a can be so great that when a specific rotational speed of the motor shaft 11 is exceeded it is bent and/or stretched outwards as a result of the centrifugal force and thereby reduces its elastic contact-pressure force on the annular leg 33 or lifts off from the latter. The former situation is desirable in order, in the case of a high-speed operation, to reduce the axial contact-pressure force and the friction at the sealing face 35. In the latter situation, namely with the lift-off, no harm is done, since during the rotation on account of the centrifugal force it is not possible for foreign matter or impurities to reach the annular gap between the annular leg 33 and the sealing lip 32a.

In the case of the present exemplary embodiment, located on the inside of the motor bearing 13 there is a ring seal 41 which is effective between the bearing races 17, 18 and has a sealing disc 42 which at its one radial edge 42a is held in an annular groove 43 of the one bearing race and by means of its other edge 42b cooperates with the other bearing race, in which case in between there can be a small annular gap 44 or this edge 42b can rest against the other bearing race with a low level of axial elastic tension. In the case of the present exemplary embodiment, the outer edge 42a of the sealing disc 42 sits in an annular groove 43 in the outer bearing race 18 and it is secured therein by means of a securing ring 46 which is inserted in an annular undercut 47 and can be made, for example, of elastic material, in which case it can be spring-deflected into the undercut 47 and thus can be latched therein. The diameter of the outer undercut edge 48 is preferably slightly larger than the outside diameter of the sealing disc 42 so that the latter can be plugged through the undercut edge 48. The sealing disc 42, preferably when it rests against the associated bearing race with axial tension, consists of an axially elastic material, in which case it can be metal, for example spring steel, or plastics material. For an electric motor 3 the sealing disc 42 is made of non-electroconductive material, such as, for example, plastics material. If, however, the annular gap 44 is large enough that a flow of electric current is prevented, the sealing disc 42 can also be made of electroconductive material. This also applies to a cage 49 that positions the anti-friction bearings or balls or rolling elements 19 and which can be made of an electroconductive material, for example metal, or of a non-electroconductive material, for example plastics material, and has radial clearance of motion at least from one of the bearing races 17, 18.

Arranged in the outer lateral surface of the outer bearing race 18 there is or are one or two annular grooves 51 that are at an axial distance from each other, in which case sitting at least in one annular groove 51 there is a ring 52 which is preferably round in cross section, is made of elastic material and in the inserted state has a larger outside diameter than the lateral surface so that it projects radially somewhat and in the assembled state presses with elastic tension against the opposing inner wall 53 of the bearing hole that receives the bearing race 18. This configuration is advantageous in two respects. On the one hand, it provides a simple and advantageous seal of the joint between the bearing race 18 and the inner wall 53. On the other hand, the elastic ring 52 bridges any radial bearing clearance or assembly clearance that exists between the bearing race 18 and the inner wall 53, thereby improving the mounting of the motor shaft 11.

It is possible for one annular groove 43 to be arranged centrally or for two annular grooves 43 to be arranged, in particular, eccentrically.

In the case of the present exemplary embodiment, the inner wall 53 of the bearing hole is located on a radial bearing wall 54 in the drive motor portion 3 that can be part of a front or rear motor socket 55, 56 which are axially screwed together and sealed at 57 and also preferably have the same outside diameter.

The invention relates not only to a drive system 3, but also to at least one motor bearing 13, 14 which is sealed or covered on one and/or both sides for protection against foreign matter or impurities and with which as a single component or structural unit the advantages which have been described above are likewise achieved.

What is claimed is:

1. An electric motor drive system for a medical or dental handpiece, said electric motor drive system comprising:

a motor housing;

a stator winding located in said motor housing;

a rotor which is secured to a motor shaft;

at least one anti-friction bearing system mounting the motor shaft in said motor housing, said bearing system including:
   an inner bearing race;
   an outer bearing race; and
   a plurality of rolling elements arranged between the bearing races; and a coupling element for coupling a dental instrument to be driven to said motor housing, said coupling element containing a coupling pin that is connected to the motor shaft and which is engagable with a drive pin of said dental instrument, said rolling elements each consisting of a non-electroconductive material.

2. A drive system according to claim 1, wherein said non-electroconductive material is a ceramic material.

3. A drive system according to claim 1, wherein said bearing races are formed from a ceramic material.

4. A dental handpiece comprising:
an instrument portion constructed to receive and mount a drill for rotation thereof;
a hose portion connected to said instrument portion for supplying at least electric current to a drill mounted thereon; and
an electric motor drive system comprising:
a motor housing;
a stator winding located in said motor housing;
a rotor which is secured to a motor shaft;
at least one anti-friction bearing system mounting the motor shaft in said motor housing, said bearing system including:
an inner bearing race;
an outer bearing race; and
a plurality of rolling elements arranged between the bearing races; and
a coupling element for coupling a dental instrument to be driven to said motor housing,
said coupling element containing a coupling pin that is connected to the motor shaft and which is engagable with a drive pin of said dental instrument,
said rolling elements each consisting of a non-electroconductive material.

5. A dental handpiece according to claim 4, wherein said non-electroconductive material is a ceramic material.

6. A dental handpiece according to claim 4, wherein said bearing races are formed from a ceramic material.

7. A dental handpiece according to claim 4, wherein said electric motor drive system is arranged within a drive system housing and said instrument portion is arranged within an instrument portion housing and wherein said electric motor drive system is connected to said instrument portion by way of a coupling which has coupling insulation consisting of an non-electroconductive material arranged to insulate said drive system housing electrically from said instrument portion housing.

8. A dental handpiece according to claim 7, wherein said coupling insulation consisting of an non-electroconductive material arranged to insulate said drive system housing electrically from said instrument portion housing comprises a plastics material.

9. An air motor drive system for a dental handpiece, said air motor drive system comprising:
a motor housing;
a rotor which is located in the motor housing and secured to a motor shaft;
at least one anti-friction bearing system mounting the motor shaft in said motor housing, said bearing system including:
an inner bearing race;
an outer bearing race; and
a plurality of rolling elements arranged between the bearing races; and
a coupling element connected to said motor housing for coupling a dental instrument to be driven to said housing,
said rolling elements each consisting of a non-electroconductive material; and
a coupling element for coupling a dental instrument to be driven to said motor housing,
said coupling element containing a coupling pin that is connected to the motor shaft and which is engagable with a drive pin of said dental instrument.

10. A drive system according to claim 9, wherein said non-electroconductive material is a ceramic material.

11. A drive system according to claim 9, wherein said bearing races are formed from a ceramic material.

12. A dental handpiece comprising:
an instrument portion constructed to receive and mount a drill for rotation thereof;
a hose portion connected to said instrument portion for supplying at least pressurized air to a drill mounted thereon; and
an air motor drive system comprising:
a motor housing;
a rotor which is located in the motor housing and secured to a motor shaft;
at least one anti-friction bearing system mounting the motor shaft in said motor housing, said bearing system including:
an inner bearing race;
an outer bearing race; and
a plurality of rolling elements arranged between the bearing races; and
a coupling element for coupling a dental instrument to be driven to said motor housing,
said coupling element containing a coupling pin that is connected to the motor shaft and which is engagable with a drive pin of said dental instrument,
said rolling elements each consisting of a non-electroconductive material; and
said coupling element containing a pin which is connected to said motor shaft for coupling said shaft to a tool mounted on such dental instrument.

13. A dental handpiece according to claim 12, wherein said non-electroconductive material is a ceramic material.

14. A dental handpiece according to claim 12, wherein said bearing races are formed from a ceramic material.

15. A dental handpiece according to claim 12, wherein said air motor drive system is arranged within a drive system housing and said instrument portion is arranged within an instrument portion housing and wherein said air motor drive system is connected to said instrument portion by way of a coupling which has coupling insulation consisting of an non-electroconductive material arranged to insulate said drive system housing electrically from said instrument portion housing.

16. A dental handpiece according to claim 15, wherein said coupling insulation consisting of an non-electroconductive material arranged to insulate said drive system housing electrically from said instrument portion housing comprises a plastics material.

* * * * *